(12) United States Patent
Quincy, III et al.

(10) Patent No.: US 7,686,840 B2
(45) Date of Patent: Mar. 30, 2010

(54) DURABLE EXOTHERMIC COATING

(75) Inventors: Roger Bradshaw Quincy, III, Cumming, GA (US); Kelly Dean Branham, Woodstock, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 594 days.

(21) Appl. No.: 11/303,005

(22) Filed: Dec. 15, 2005

(65) Prior Publication Data

US 2007/0141929 A1 Jun. 21, 2007

(51) Int. Cl.
A61F 7/08 (2006.01)
(52) U.S. Cl. .................. 607/96; 607/108; 607/113; 428/340
(58) Field of Classification Search .................. 442/59; 607/96, 108, 113; 428/340
See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 3,901,236 A | 8/1975 | Assarsson et al. | |
| 3,939,838 A | 2/1976 | Fujinami et al. | |
| 4,076,663 A | 2/1978 | Masuda et al. | |
| 4,100,324 A | 7/1978 | Anderson et al. | |
| 4,286,082 A | 8/1981 | Tsubakimoto et al. | |
| 4,323,534 A | 4/1982 | DesMarais | |
| 4,340,563 A | 7/1982 | Appel et al. | |
| 4,341,216 A | 7/1982 | Obenour | |
| 4,423,118 A | 12/1983 | Corbett et al. | |
| 4,663,220 A | 5/1987 | Wisneski et al. | |
| 4,758,239 A | 7/1988 | Yeo et al. | |
| 4,834,738 A | 5/1989 | Kielpikowski et al. | |
| 5,093,422 A | 3/1992 | Himes | |
| 5,161,686 A | 11/1992 | Weber et al. | |
| 5,213,881 A | 5/1993 | Timmons et al. | |

(Continued)

FOREIGN PATENT DOCUMENTS

EP 0348978 A2 1/1990

(Continued)

OTHER PUBLICATIONS

Search Report and Written Opinion for PCT/US2006/046692, May 25, 2007.

(Continued)

*Primary Examiner*—D. Lawrence Tarazano
*Assistant Examiner*—Matthew D Matzek
(74) *Attorney, Agent, or Firm*—Dority & Manning, P.A.

(57) ABSTRACT

A substrate that contains an exothermic coating is provided. More specifically, the exothermic coating includes one or more components (e.g., carbon, oxidizable metal, moisture-retaining particles, etc.) that are durably adhered to the substrate. To provide the desired durability, the exothermic coating includes the combination of a certain amount of a polymer latex and polysaccharide. When appropriately selected and incorporated into the exothermic coating, the present inventors have discovered that these components may interact synergistically to improve binding capacity.

24 Claims, 2 Drawing Sheets

U.S. PATENT DOCUMENTS

| | | | |
|---|---|---|---|
| 5,272,236 A | 12/1993 | Lai et al. |
| 5,278,272 A | 1/1994 | Lai et al. |
| 5,284,703 A | 2/1994 | Everhart et al. |
| 5,304,599 A | 4/1994 | Himes |
| 5,306,487 A | 4/1994 | Karapasha et al. |
| 5,316,837 A | 5/1994 | Cohen |
| 5,332,613 A | 7/1994 | Taylor et al. |
| 5,350,624 A | 9/1994 | Georger et al. |
| 5,382,400 A | 1/1995 | Pike et al. |
| 5,418,945 A | 5/1995 | Carter et al. |
| 5,539,056 A | 7/1996 | Yang et al. |
| 5,540,916 A | 7/1996 | Parks |
| 5,562,994 A | 10/1996 | Abba et al. |
| 5,596,052 A | 1/1997 | Resconi et al. |
| 5,599,585 A | 2/1997 | Cohen |
| 5,628,737 A | 5/1997 | Dobrin et al. |
| 5,656,355 A | 8/1997 | Cohen |
| 5,693,385 A | 12/1997 | Parks |
| 5,834,114 A | 11/1998 | Economy et al. |
| 5,836,932 A | 11/1998 | Buell et al. |
| 5,843,057 A | 12/1998 | McCormack |
| 5,855,999 A | 1/1999 | McCormack |
| 5,879,378 A | 3/1999 | Usui |
| 5,906,879 A | 5/1999 | Huntoon et al. |
| 5,932,497 A | 8/1999 | Morman et al. |
| 5,984,995 A | 11/1999 | White |
| 5,997,981 A | 12/1999 | McCormack et al. |
| 6,002,064 A | 12/1999 | Kobylivker et al. |
| 6,015,764 A | 1/2000 | McCormack et al. |
| 6,019,782 A | 2/2000 | Davis et al. |
| 6,037,281 A | 3/2000 | Mathis et al. |
| 6,099,556 A | 8/2000 | Usui |
| 6,111,163 A | 8/2000 | McCormack et al. |
| 6,114,024 A | 9/2000 | Forte |
| 6,149,934 A | 11/2000 | Krzysik et al. |
| 6,153,209 A | 11/2000 | Vega et al. |
| 6,197,045 B1 | 3/2001 | Carson |
| 6,198,018 B1 | 3/2001 | Curro |
| 6,203,810 B1 | 3/2001 | Alemany et al. |
| 6,245,401 B1 | 6/2001 | Ying et al. |
| 6,420,625 B1 | 7/2002 | Jones et al. |
| 6,436,128 B1 | 8/2002 | Usui |
| 6,461,457 B1 | 10/2002 | Taylor et al. |
| 6,517,906 B1 | 2/2003 | Economy et al. |
| 6,573,212 B2 | 6/2003 | McCrae et al. |
| 6,576,810 B1 | 6/2003 | Underhill et al. |
| 6,639,004 B2 | 10/2003 | Falat et al. |
| 6,713,414 B1 | 3/2004 | Pomplun et al. |
| 6,770,064 B1 | 8/2004 | Ruscher |
| 6,794,024 B1 | 9/2004 | Walton et al. |
| 2002/0161420 A1 | 10/2002 | Usui |
| 2004/0166248 A1 | 8/2004 | Hu et al. |
| 2004/0178384 A1 | 9/2004 | Usui |
| 2005/0098466 A1 | 5/2005 | Thomas |
| 2005/0113771 A1 | 5/2005 | MacDonald et al. |
| 2006/0141882 A1 | 6/2006 | Quincy, III et al. |
| 2006/0142712 A1 | 6/2006 | Quincy, III |
| 2006/0142828 A1 | 6/2006 | Schorr et al. |

FOREIGN PATENT DOCUMENTS

| | | |
|---|---|---|
| EP | 0370600 A1 | 5/1990 |
| WO | 9829079 | 7/1998 |

OTHER PUBLICATIONS

Article—*Adsorption of Gases in Multimolecular Layers*, Brunauer et al., The Journal of the American Chemical Society, vol. 60, Jan.-Jun. 1938, pp. 309-319.

DURABLE EXOTHERMIC COATING

BACKGROUND OF THE INVENTION

Certain metal powders (e.g., iron powder) are oxidized in the presence of air and moisture. Because the oxidation reaction is exothermic and generates heat, the metal powders have been incorporated into exothermic compositions to provide warmth. For example, conventional exothermic compositions contained a metal powder, activated carbon, and metal halide. The activated carbon acted as a catalyst to facilitate the exothermic reaction, while the metal halide removed surface oxide films on the metal powder to allow the reaction to proceed to a sufficient extent. Unfortunately, various problems existed when attempting to apply such exothermic compositions to a substrate. Specifically, if the exothermic composition were exposed to moisture during application, the exothermic reaction could occur prematurely. This ultimately would lower the quality of the exothermic composition and give rise to various other problems, such as an increased difficulty in handling due to coagulation.

Various techniques were developed in an attempt to overcome these and other problems. For example, U.S. Pat. No. 6,436,128 to Usui describes an exothermic composition that contains an exothermic substance, a water-absorptive polymer and/or tackifier, a carbon component and/or metal halide, and water. An excessive amount of water is used in the composition to suppress a premature oxidation reaction with air. Once formulated, the exothermic composition of Usui is laminated and sealed in a thin pouch. The pouch absorbs water from the composition so that, when the seal is broken, the exothermic reaction may proceed upon exposure to air and moisture. However, devices such as described above still possess a variety of problems. For example, certain components of the exothermic composition are often in particle form (e.g., carbon and exothermic substance). Unfortunately, these particles may rub off over time, thereby reducing the heat-producing characteristics of the device.

As such, a need currently exists for an improved technique for durably adhering an exothermic coating to a substrate that is simple, effective, and relatively inexpensive.

SUMMARY OF THE INVENTION

In accordance with one embodiment of the present invention, a substrate containing an exothermic coating is disclosed that is activatable in the presence of oxygen and moisture to generate heat. The exothermic coating comprises a polymer latex and polysaccharide, the polymer latex having a glass transition temperature of about 30° C. or less. The polymer latex constitutes from about 0.01 wt. % to about 20 wt. % of the exothermic coating and the polysaccharide constitutes from about 0.01 wt. % to about 20 wt. % of the exothermic coating. The weight ratio of the polymer latex to the polysaccharide is from about 0.5:1 to about 5:1.

In accordance with another embodiment of the present invention, a method for applying an exothermic coating to a substrate is disclosed. The method comprises forming a coating formulation that comprises an oxidizable metal powder, polymer latex, polysaccharide, and solvent. The solvent constitutes from about 10 wt. % to about 80 wt. % of the coating formulation, the polymer latex constitutes from about 0.01 wt. % to about 20 wt. % of the coating formulation, and the polysaccharide constitutes from about 0.01 wt. % to about 20 wt. % of the coating formulation. The coating formulation is applied to the substrate, and the coated substrate is heated.

Other features and aspects of the present invention are described in more detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

DETAILED DESCRIPTION OF REPRESENTATIVE EMBODIMENTS

Definitions

Figure 1:
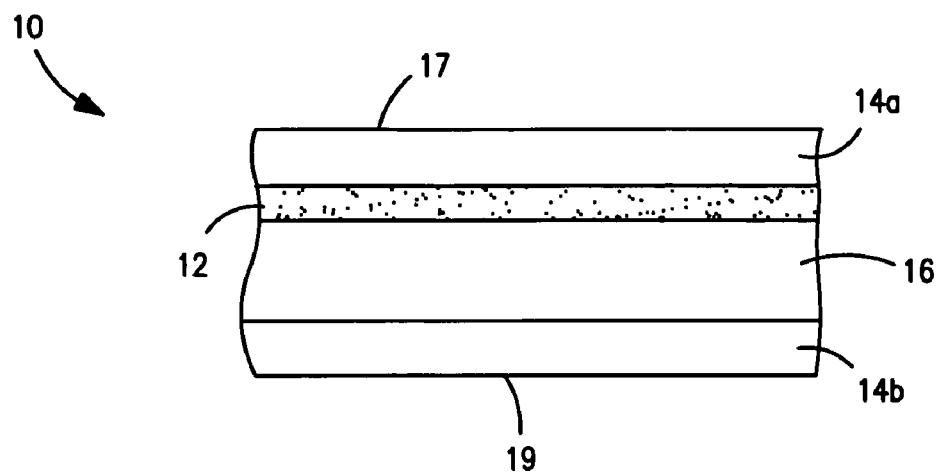
FIG. 1 illustrates a cross-sectional view of one embodiment of a thermal device that may be formed according to the present invention.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, bonded carded web processes, etc.

As used herein, the term "meltblowing" refers to a process in which fibers are formed by extruding a molten thermoplastic material through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that may be continuous or discontinuous, are generally smaller than 10 microns in diameter, and are generally tacky when deposited onto a collecting surface.

As used herein, the term "spunbonding" refers to a process in which small diameter substantially continuous fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spun-bonded nonwoven webs is described and illustrated, for example, in U.S. Pat. Nos. 4,340,563 to Appel, et al., 3,692,618 to Dorschner, et al., 3,802,817 to Matsuki, et al., 3,338,992 to Kinney, 3,341,394 to Kinney, 3,502,763 to Hartman, 3,502,538 to Levy, 3,542,615 to Dobo, et al., and 5,382,400 to Pike, et al., which are incorporated herein in their entirety by reference thereto for all purposes. Spunbonded fibers are generally not tacky when they are deposited onto a collecting surface. Spunbonded fibers may sometimes have diameters less than about 40 microns, and are often between about 5 to about 20 microns.

As used herein, the term "coform" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. Nos. 4,100,324 to Anderson, et al.; 5,284,703 to Everhart, et al.; and 5,350,624 to Georger, et al.; which are incorporated herein in their entirety by reference thereto for all purposes.

As used herein, the "water vapor transmission rate" (WVTR) generally refers to the rate at which water vapor permeates through a material as measured in units of grams per meter squared per 24 hours ($g/m^2/24$ hrs). The test used to determine the WVTR of a material may vary based on the nature of the material. For instance, in some embodiments, WVTR may be determined in general accordance with ASTM Standard E-96E-80. This test may be particularly well suited for materials thought to have a WVTR of up to about 3,000 $g/m^2/24$ hrs. Another technique for measuring WVTR involves the use of a PERMATRAN-W 100K water vapor permeation analysis system, which is commercially available from Modern Controls, Inc. of Minneapolis, Minn. Such a system may be particularly well suited for materials thought to have a WVTR of greater than about 3,000 $g/m^2/24$ hrs. However, as is well known in the art, other systems and techniques for measuring WVTR may also be utilized.

As used herein, the term "breathable" means pervious to water vapor and gases, but impermeable to liquid water. For instance, "breathable barriers" and "breathable films" allow water vapor to pass therethrough, but are substantially impervious to liquid water. The "breathability" of a material is measured in terms of water vapor transmission rate (WVTR), with higher values representing a more vapor-pervious material and lower values representing a less vapor-pervious material. Breathable materials may, for example, have a water vapor transmission rate (WVTR) of at least about 100 grams per square meter per 24 hours ($g/m^2/24$ hours), in some embodiments from about 500 to about 20,000 $g/m^2/24$ hours, and in some embodiments, from about 1,000 to about 15,000 $g/m^2/24$ hours.

DETAILED DESCRIPTION

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

Generally speaking, the present invention is directed to a substrate that contains an exothermic coating. More specifically, the exothermic coating includes one or more components (e.g., carbon, oxidizable metal, moisture-retaining particles, etc.) that are durably adhered to the substrate. To provide the desired durability, the exothermic coating includes the combination of a certain amount of a polymer latex and polysaccharide. When appropriately selected and incorporated into the exothermic coating, the present inventors have discovered that these components may interact synergistically to improve binding capacity.

The polymer latex used in the present invention may be in the form of a polymer emulsion or dispersion that contains polymer particles dispersed in water and stabilized with surface active ingredients (e.g., low molecular weight emulsifiers or high molecular weight protective colloids). The polymer latex typically has a glass transition temperature of about 30° C. or less so that the flexibility of the resulting substrate is not substantially restricted. Moreover, the polymer latex also typically has a glass transition temperature of about −25° C. or more to minimize the tackiness of the polymer latex. In some embodiments, the polymer has a glass transition temperature from about −15° C. to about 15° C., and in some embodiments, from about −10° C. to about 0° C. The polymer latex may also have an average molecular weight that varies depending on the ultimate use of the polymer. Desirably, the polymer latex has a weight average molecular weight ranging from about 500,000 to about 200,000,000, and in some embodiments, from about 500,000 to about 100,000,000.

Some suitable polymer latexes that may be utilized in the present invention may be based on polymers such as, but are not limited to, styrene-butadiene copolymers, polyvinyl acetate homopolymers, vinyl-acetate ethylene copolymers, vinyl-acetate acrylic copolymers, ethylene-vinyl chloride copolymers, ethylene-vinyl chloride-vinyl acetate terpolymers, acrylic polyvinyl chloride polymers, styrene-acrylic copolymers, acrylic polymers, nitrile polymers, and any other suitable anionic polymer latex polymers known in the art. Particularly suitable polymer latexes include, but are not limited to, ethylene-vinyl acetate copolymers, styrene-butadiene copolymers, and ethylene-vinyl chloride copolymers. The polymer latex may have a net positive or negative charge, as well as a net charge that is generally neutral. The charge of the polymer latexes described above may be readily varied, as is well known in the art, by utilizing a stabilizing agent having the desired charge during preparation of the polymer latex.

In most cases, the polymer latex is crosslinked so that it is water-insoluble and capable of functioning as a binder. Crosslinking may be performed using any known technique in the art, such as by heating, ionization, etc. Preferably, the polymer latex is self-crosslinking in that external crosslinking agents (e.g., N-methylol acrylamide) are not required to induce crosslinking. Specifically, crosslinking agents may lead to the formation of bonds between the polymer latex and the substrate to which it is applied. Such bonding may sometimes interfere with the effectiveness of the substrate in generating heat. Thus, the polymer latex may be substantially free of crosslinking agents. Particularly suitable self-crosslinking polymer latexes are ethylene-vinyl acetate copolymers available from Celanese Corp. of Dallas, Tex. under the designation DUR-O-SET® Elite (e.g., PE-25220A). Alternatively, an inhibitor may simply be employed that reduces the extent of crosslinking, such as free radical scavengers, methyl hydroquinone, t-butylcatechol, pH control agents (e.g., potassium hydroxide), etc.

In addition to the polymer latex, the exothermic coating of the present invention also contains other components that enhance durability. For example, the exothermic coating contains a polysaccharide that increases the viscosity of the coating formulation to inhibit settling and particle agglomeration. The polysaccharide may also aid in binding particles to the substrate. As used herein, the term "polysaccharide" includes any polymer containing carbohydrate units, which may be cationic, anionic, nonionic, and/or amphoteric. Some suitable polysaccharides include natural gums, such as gellan gum and alginate gums (e.g., ammonium and alkali metal of salts of alginic acid); chitosan; carboxymethylcellulose, pectins, carrageenan, xantham gum, and derivatives or salts thereof. The particular type of polysaccharide selected will depend, in part, on the nature of exothermic coating and the components used therein. Specifically, the charge of the polysaccharide is either neutral (e.g., nonionic) or the same as the charge of the polymer latex (e.g., cationic or anionic) to reduce the likelihood of agglomeration. For example, the polymer latex may be anionic (e.g., ethylene vinyl-acetate) and the polysaccharide may be nonionic.

One particular class of suitable nonionic polysaccharides includes nonionic cellulosic ethers. Suitable nonionic cellulosic ethers may include, but are not limited to, alkyl cellulose ethers, such as methyl cellulose and ethyl cellulose; hydroxyalkyl cellulose ethers, such as hydroxyethyl cellulose, hydroxypropyl cellulose, hydroxypropyl hydroxybutyl cellulose, hydroxyethyl hydroxypropyl cellulose, hydroxyethyl hydroxybutyl cellulose and hydroxyethyl hydroxypropyl hydroxybutyl cellulose; alkyl hydroxyalkyl cellulose ethers, such as methyl hydroxyethyl cellulose, methyl hydroxypropyl cellulose, ethyl hydroxyethyl cellulose, ethyl hydroxypropyl cellulose, methyl ethyl hydroxyethyl cellulose and methyl ethyl hydroxypropyl cellulose; and so forth. The cellulosic ethers may include, for instance, those available from Akzo Nobel of Stamford, Conn. under the name "BERMOCOLL." Still other suitable cellulosic ethers are those available from Shin-Etsu Chemical Co., Ltd. of Tokyo, Japan under the name "METOLOSE", including METOLOSE Type SM (methycellulose), METOLOSE Type SH (hydroxypropylmethyl cellulose), and METOLOSE Type SE (hydroxyethylmethyl cellulose). One particular example of a suitable nonionic cellulosic ether is methylcellulose having a degree of methoxyl substitution (DS) of 1.8. The degree of methoxyl substitution represents the average number of hydroxyl groups present on each anhydroglucose unit that have been reacted, which may vary between 0 and 3. One such cellulosic ether is METOLOSE SM-100, which is a methylcellulose commercially available from Shin-Etsu Chemical Co., Ltd. Other suitable cellulosic ethers are also available from Hercules, Inc. of Wilmington, Del. under the name "CULMINAL."

The polymer latex and polysaccharide concentrations in the coating may generally vary depending on the desired properties of the resulting substrate. For instance, high latex concentrations may provide better physical properties for the coated substrate, but may likewise have an adverse affect on other properties, such as the flexibility of the substrate to which it is applied. Conversely, high polysaccharide concentrations may not provide the desired degree of durability. To provide the optimum binding properties for the coating, the weight ratio of the polymer latex to the polysaccharide typically ranges from about 0.5:1 to about 5:1, in some embodiments, from about 1:1 to about 3:1, and in some embodiments, from about 1.5:1 to about 3:1. Further, the polymer latex concentration is typically from about 0.01 to about 20 wt. %, in some embodiments from about 0.5 wt. % to about 10 wt. %, and in some embodiments, from about 0.5 wt. % to about 5 wt. % of the exothermic coating. Likewise, the polysaccharide concentration is typically from about 0.01 to about 20 wt. %, in some embodiments from about 0.1 wt. % to about 15 wt. %, and in some embodiments, from about 0.5 wt. % to about 8 wt. % of the exothermic coating.

As stated above, the exothermic coating also contains other components that provide the desired heating characteristics to the substrate. For example, the exothermic coating may contain an oxidizable metal, such as iron, zinc, aluminum, magnesium, and so forth. The metal may be initially provided in particulate or powder form to facilitate handling and to reduce costs. Various methods for removing impurities from a crude metal (e.g. iron) to form a powder include, for example, wet processing techniques, such as solvent extraction, ion exchange, and electrolytic refining for separation of metallic elements; hydrogen gas ($H_2$) processing for removal of gaseous elements, such as oxygen and nitrogen; floating zone melting refining method. Using such techniques, the metal purity may be at least about 95%, in some embodiments at least about 97%, and in some embodiments, at least about 99%. The particle size of the metal powder may also be less than about 500 micrometers, in some embodiments less than about 100 micrometers, and in some embodiments, less than about 50 micrometers. The use of such small particles may enhance the contact surface of the metal with air, thereby improving the likelihood and efficiency of the desired exothermal reaction. The concentration of the metal powder employed may generally vary depending on the nature of the metal powder, and the desired extent of the exothermal/oxidation reaction. In most embodiments, the metal powder is present in the exothermic coating in an amount from about 40 wt. % to about 95 wt. %, in some embodiments from about 50 wt. % to about 90 wt. %, and in some embodiments, from about 60 wt. % to about 80 wt. %.

A carbon component may also be utilized in the exothermic coating. Without intending to be limited in theory, it is believed that such a carbon component promotes the oxidation reaction of the metal and acts as a catalyst for generating heat. The carbon component may in the form of particles and contain activated carbon, carbon black, graphite, and so forth. When utilized, activated carbon may be formed from sawdust, wood, charcoal, peat, lignite, bituminous coal, coconut shells, etc. Some suitable forms of activated carbon and techniques for formation thereof are described in U.S. Pat. Nos. 5,693,385 to Parks; 5,834,114 to Economy, et al.; 6,517,906 to Economy, et al.; 6,573,212 to McCrae, et al., as well as U.S. Patent Application Publication Nos. 2002/0141961 to Falat, et al. and 2004/0166248 to Hu, et al., all of which are incorporated herein in their entirety by reference thereto for all purposes. Activated carbon may be present in the coating (prior to drying) in an amount from about 1 wt. % to about 50 wt. %, in some embodiments from about 2 wt. % to about 30 wt. %, and in some embodiments, from about 5 wt. % to about 20 wt. %.

Other particles may also be employed in the exothermic coating that function as moisture retainers. That is, prior to the oxidation/exothermic reaction, these particles may retain moisture. However, after the reaction has proceeded to a certain extent and the moisture concentration is reduced, the particles may release the moisture to allow the reaction to continue. Besides acting as a moisture retainer, the particles may also provide other benefits to the exothermic coating of the present invention. For example, the particles may alter the black color normally associated with the carbon component and/or metal powder. When utilized, the size of the moisture-retaining particles may be less than about 500 micrometers, in some embodiments less than about 100 micrometers, and in some embodiments, less than about 50 micrometers. Likewise, the particles may be porous. Without intending to be limited by theory, it is believed that porous particles may provide a passage for air and/or water vapors to better contact the metal powder. For example, the particles may have pores/channels with a mean diameter of greater than about 5 angstroms, in some embodiments greater than about 20 angstroms, and in some embodiments, greater than about 50 angstroms. The surface area of such particles may also be greater than about 15 square meters per gram, in some embodiments greater than about 25 square meters per gram, and in some embodiments, greater than about 50 square meters per gram. Surface area may be determined by the physical gas adsorption (B.E.T.) method of Bruanauer, Emmet, and Teller, *Journal of American Chemical Society*, Vol. 60, 1938, p. 309, with nitrogen as the adsorption gas.

In one particular embodiment, porous carbonate particles (e.g., calcium carbonate) are used to retain moisture and also to alter the black color normally associated with activated carbon and/or metal powder. Such a color change may be more aesthetically pleasing to a user, particularly when the coating is employed on substrates designed for consumer/personal use. Suitable white calcium carbonate particles are commercially available in both dry and aqueous slurry form from Omya, Inc. of Proctor, Vt. Still other suitable inorganic particles that may retain moisture include, but are not limited to, silicates, such as calcium silicate, alumina silicates (e.g., mica powder, clay, etc.), magnesium silicates (e.g., talc), quartzite, calcium silicate fluorite, vermiculite, etc.; alumina; silica; and so forth. The concentration of the particles may generally vary depending on the nature of the particles, and the desired extent of exothermic reaction and color alteration. For instance, the particles may be present in the exothermic coating in an amount from about 0.01 wt. % to about 30 wt. %, in some embodiments from about 0.1 wt. % to about 20 wt. %, and in some embodiments, from about 1 wt. % to about 15 wt. %.

Still other components may also be employed in the exothermic coating. For example, as is well known in the art, an electrolytic salt may be employed to react with and remove any passivating oxide layer(s) that might otherwise prevent the metal from oxidizing. Suitable electrolytic salts may include, but are not limited to, alkali halides or sulfates, such as sodium chloride, potassium chloride, etc.; alkaline halides or sulfates, such as calcium chloride, magnesium chloride, etc., and so forth. When employed, the electrolytic salt is typically present in the exothermic coating in an amount from about 0.01 wt. % to about 10 wt. %, in some embodiments from about 0.1 wt. % to about 8 wt. %, and in some embodiments, from about 1 wt. % to about 6 wt. %. In addition to the above-mentioned components, other components, such as surfactants, pH adjusters, dyes/pigments/inks, etc., may also be included in the exothermic coating of the present invention. Although not required, such additional components typically constitute less than about 5 wt. %, in some embodiments less than about 2 wt. %, and in some embodiments, from about 0.001 wt. % to about 1 wt. % of the exothermic coating.

Regardless of the manner in which it is formed, the exothermic coating is applied to a substrate, which may perform other functions of a thermal device or simply act as a physical carrier for the coating. Any type of substrate may be applied with the exothermic coating in accordance with the present invention. For instance, nonwoven fabrics, woven fabrics, knit fabrics, paper web, film, foams, etc., may be applied with the exothermic coating. When utilized, the nonwoven fabrics may include, but are not limited to, spunbonded webs (apertured or non-apertured), meltblown webs, bonded carded webs, air-laid webs, coform webs, hydraulically entangled webs, and so forth. Typically, the polymers used to form the substrate have a softening or melting temperature that is higher than the temperature needed to evaporate moisture. One or more components of such polymers may have, for instance, a softening temperature of from about 100° C. to about 400° C., in some embodiments from about 110° C. to about 300° C., and in some embodiments, from about 120° C. to about 250° C. Examples of such polymers may include, but are not limited to, synthetic polymers (e.g., polyethylene, polypropylene, polyethylene terephthalate, nylon 6, nylon 66, KEVLAR™, syndiotactic polystyrene, liquid crystalline polyesters, etc.); cellulosic polymers (softwood pulp, hardwood pulp, thermomechanical pulp, etc.); combinations thereof; and so forth.

To apply the exothermic coating to a substrate, the components may initially be dissolved or dispersed in a solvent. For example, one or more of the above-mentioned components may be mixed with a solvent, either sequentially or simultaneously, to form a coating formulation that may be easily applied to a substrate. Any solvent capable of dispersing or dissolving the components is suitable, for example water; alcohols such as ethanol or methanol; dimethylformamide; dimethyl sulfoxide; hydrocarbons such as pentane, butane, heptane, hexane, toluene and xylene; ethers such as diethyl ether and tetrahydrofuran; ketones and aldehydes such as acetone and methyl ethyl ketone; acids such as acetic acid and formic acid; and halogenated solvents such as dichloromethane and carbon tetrachloride; as well as mixtures thereof. In one particular embodiment, for example, water is used as the solvent so that an aqueous coating formulation is formed. The concentration of the solvent is generally high enough to inhibit oxidization of the metal prior to use. Specifically, when present in a high enough concentration, the solvent may act as a barrier to prevent air from prematurely contacting the oxidizable metal. If the amount of solvent is too small, however, the exothermic reaction may occur prematurely. Likewise, if the amount of solvent is too large, the amount of metal deposited on the substrate might be too low to provide the desired exothermal effect. Although the actual concentration of solvent (e.g., water) employed will generally depend on the type of oxidizable metal and the substrate on which it is applied, it is nonetheless typically present in an amount from about 10 wt. % to about 80 wt. %, in some embodiments from about 20 wt. % to about 70 wt. %, and in some embodiments, from about 25 wt. % to about 60 wt. % of the coating formulation.

The amount of the other components added to the coating formulation may vary depending on the amount of heat desired, the wet pick-up of the application method utilized, etc. For example, the amount of the oxidizable metal (in powder form) within the coating formulation generally ranges from about 20 wt. % to about 80 wt. %, in some embodiments from about 30 wt. % to about 70 wt. %, and in some embodiments, from about 35 wt. % to about 60 wt. %. In addition, the carbon component may constitute from about 0.1 wt. % to about 20 wt. %, in some embodiments from about 0.1 wt. % to about 15 wt. %, and in some embodiments, from about 0.2 wt. % to about 10 wt. %. of the coating formulation. Polymer latexes may constitute from about 0.01 wt. % to about 20 wt. %, in some embodiments from about 0.5 wt. % to about 15 wt. %, and in some embodiments, from about 1 wt. % to about 10 wt. % of the coating formulation. Polysaccharides may constitute from about 0.01 wt. % to about 20 wt. %, in some embodiments from about 0.5 wt. % to about 15 wt. %, and in some embodiments, from about 1 wt. % to about 10 wt. % of the coating formulation. Electrolytic salts may constitute from about 0.01 wt. % to about 10 wt. %, in some embodiments from about 0.1 wt. % to about 8 wt. %, and in some embodiments, from about 1 wt. % to about 5 wt. %. of the coating formulation. Further, moisture-retaining particles (e.g., calcium carbonate) may constitute from about 2 wt. % to about 30 wt. %, in some embodiments from about 3 wt. % to about 25 wt. %, and in some embodiments, from about 4 wt. % to about 10 wt. %. of the coating formulation. Other components, such as surfactants, pH adjusters, etc., may also constitute from about 0.001 wt. % to about 0.5 wt. %, in some embodiments from about 0.01 wt. % to about 0.1 wt. %, and in some embodiments from about 0.02 wt. % to about 0.08 wt. % of the coating formulation.

The solids content and/or viscosity of the coating formulation may be varied to achieve the desired amount of heat generation. For example, the coating formulation may have a solids content of from about 30% to about 80%, in some embodiments from about 40% to about 70%, and in some embodiments, from about 50% to about 60%. By varying the solids content of the coating formulation, the presence of the metal powder and other components in the exothermic coating may be controlled. For example, to form an exothermic coating with a higher level of metal powder, the coating formulation may be provided with a relatively high solids content so that a greater percentage of the metal powder is incorporated into the exothermic coating during the application process. In addition, the viscosity of the coating formulation may also vary depending on the coating method and/or type of binder employed. For instance, lower viscosities may be employed for saturation coating techniques (e.g., dip-coating), while higher viscosities may be employed for drop-coating techniques. Generally, the viscosity is less than about $2 \times 10^6$ centipoise, in some embodiments less than about $2 \times 10^5$ centipoise, in some embodiments less than about $2 \times 10^4$ centipoise, and in some embodiments, less than about $2 \times 10^3$ centipoise, such as measured with a Brookfield DV-1 viscometer with an LV spindle.

The coating formulation may be applied to a substrate using any conventional technique, such as bar, roll, knife, curtain, print (e.g., rotogravure), spray, slot-die, drop-coating, or dip-coating techniques. The materials that form the substrate (e.g., fibers) may be coated before and/or after incorporation into the substrate. The coating may be applied to one or both surfaces of the substrate. For example, the exothermic coating may be present on a surface of the substrate that is opposite to that facing the wearer or user to avoid the possibility of burning. In addition, the coating formulation may cover an entire surface of the substrate, or may only cover a portion of the surface. When applying the exothermic coating to multiple surfaces, each surface may be coated sequentially or simultaneously.

Regardless of the manner in which the coating is applied, the resulting thermal substrate is typically heated to a certain temperature to remove the solvent and any moisture from the coating. For example, the thermal substrate may be heated to a temperature of at least about 100° C., in some embodiments at least about 10° C., and in some embodiments, at least about 120° C. In this manner, the resulting dried exothermic coating is anhydrous, i.e., generally free of water. By minimizing the amount of moisture, the exothermic coating is less likely to react prematurely and generate heat. That is, the oxidizable metal does not generally react with oxygen unless some minimum amount of water is present. Thus, the exothermic coating may remain inactive until placed in the vicinity of moisture (e.g., next to a layer that contains moisture) during use. It should be understood, however, that relatively small amounts of water may still be present in the exothermic coating without causing a substantial exothermic reaction. In some embodiments, for example, the exothermic coating contains water in an amount less than about 0.5% by weight, in some embodiments less than about 0.1% by weight, and in some embodiments, less than about 0.01% by weight.

The solids add-on level of the exothermic coating may also be varied as desired. The "solids add-on level" is determined by subtracting the weight of the untreated substrate from the weight of the treated substrate (after drying), dividing this calculated weight by the weight of the untreated substrate, and then multiplying by 100%. Lower add-on levels may optimize certain properties (e.g., absorbency), while higher add-on levels may optimize heat generation. In some embodiments, for example, the add-on level is from about 100% to about 5000%, in some embodiments from about 200% to about 2400%, and in some embodiments, from about 400% to about 1200%. The thickness of the exothermic coating may also vary. For example, the thickness may range from about 0.01 millimeters to about 5 millimeters, in some embodiments, from about 0.01 millimeters to about 3 millimeters, and in some embodiments, from about 0.1 millimeters to about 2 millimeters. In some cases, a relatively thin coating may be employed (e.g., from about 0.01 millimeters to about 0.5 millimeters). Such a thin coating may enhance the flexibility of the substrate, while still providing uniform heating.

To maintain absorbency, porosity, flexibility, and/or some other characteristic of the substrate, it may sometimes be desired to apply the exothermic coating so as to cover less than 100%, in some embodiments from about 10% to about 80%, and in some embodiments, from about 20% to about 60% of the area of one or more surfaces of the substrate. For instance, in one particular embodiment, the exothermic coating is applied to the substrate in a preselected pattern (e.g., reticular pattern, diamond-shaped grid, dots, and so forth). Although not required, such a patterned exothermic coating may provide sufficient warming to the substrate without covering a substantial portion of the surface area of the substrate. This may be desired to optimize flexibility, absorbency, or other characteristics of the substrate. It should be understood, however, that the coating may also be applied uniformly to one or more surfaces of the substrate. In addition, a patterned exothermic coating may also provide different functionality to each zone. For example, in one embodiment, the substrate is treated with two or more patterns of coated regions that may or may not overlap. The regions may be on the same or different surfaces of the substrate. In one embodiment, one region of a substrate is coated with a first exothermic coating, while another region is coated with a second exothermic coating. If desired, one region may provide a different amount of heat than another region.

Besides having functional benefits, the thermal substrate may also have various aesthetic benefits as well. For example, although containing activated carbon, the thermal substrate may be made without the black color commonly associated with activated carbon. In one embodiment, white or light-colored particles (e.g., calcium carbonate, titanium dioxide, etc.) are employed in the exothermic coating so that the resulting substrate has a grayish or bluish color. In addition, various pigments, dyes, and/or inks may be employed to alter the color of the exothermic coating. The substrate may also be applied with patterned regions of the exothermic coating to form a substrate having differently colored regions.

Other substrates may also be employed to improve the exothermic properties of the thermal substrate. For example, a first thermal substrate may be employed in conjunction with a second thermal substrate. The substrates may function together to provide heat to a surface, or may each provide heat to different surfaces. In addition, substrates may be employed that are not applied with the exothermic coating of the present invention, but instead applied with a coating that simply facilitates the reactivity of the exothermic coating. For example, a substrate may be used near or adjacent to the thermal substrate of the present invention that includes a coating of moisture-retaining particles. As described above, the moisture-retaining particles may retain and release moisture for activating the exothermic reaction.

As indicated above, moisture and oxygen are supplied to the exothermic coating to activate the exothermic reaction. To provide the desired heating profile, the rate at which moisture is allowed to contact the exothermic coating may be selectively controlled in accordance with the present invention. Namely, if too much moisture is supplied within a given time period, the exothermic reaction may produce an excessive amount of heat that overly warms or burns the user. On the other hand, if too little moisture is supplied within a given time period, the exothermic reaction may not be sufficiently activated. The desired application rate may of course be achieved by manually applying the desired amount of moisture, e.g., by hand or with the aid of external equipment, such as a syringe. Alternatively, the thermal device itself may contain a mechanism for controlling the moisture release rate.

One technique for using the thermal device as a mechanism for controlling the moisture application rate involves the use of a moisture-holding layer. The moisture-holding layer may be employed in the thermal device to hold moisture and controllably release it to the exothermic composition over an extended period of time. The moisture-holding layer may include an absorbent web formed using any technique, such as a dry-forming technique, an airlaying technique, a carding technique, a meltblown or spunbond technique, a wet-forming technique, a foam-forming technique, etc. In an airlaying process, for example, bundles of small fibers having typical lengths ranging from about 3 to about 19 millimeters are separated and entrained in an air supply and then deposited onto a forming screen, usually with the assistance of a vacuum supply. The randomly deposited fibers then are bonded to one another using, for example, hot air or an adhesive.

The moisture-holding layer typically contains cellulosic fibers, such as natural and/or synthetic fluff pulp fibers. The fluff pulp fibers may be kraft pulp, sulfite pulp, thermomechanical pulp, etc. In addition, the fluff pulp fibers may include high-average fiber length pulp, low-average fiber length pulp, or mixtures of the same. One example of suitable high-average length fluff pulp fibers includes softwood kraft pulp fibers. Softwood kraft pulp fibers are derived from coniferous trees and include pulp fibers such as, but not limited to, northern, western, and southern softwood species, including redwood, red cedar, hemlock, Douglas-fir, true firs, pine (e.g., southern pines), spruce (e.g., black spruce), combinations thereof, and so forth. Northern softwood kraft pulp fibers may be used in the present invention. One example of commercially available southern softwood kraft pulp fibers suitable for use in the present invention include those available from Weyerhaeuser Company with offices in Federal Way, Wash. under the trade designation of "NB-416." Another type of fluff pulp that may be used in the present invention is identified with the trade designation CR1654, available from U.S. Alliance of Childersburg, Ala., and is a bleached, highly absorbent sulfate wood pulp containing primarily softwood fibers. Still another suitable fluff pulp for use in the present invention is a bleached, sulfate wood pulp containing primarily softwood fibers that is available from Bowater Corp. with offices in Greenville, S.C. under the trade name CoosAbsorb S pulp. Low-average length fibers may also be used in the present invention. An example of suitable low-average length pulp fibers is hardwood kraft pulp fibers. Hardwood kraft pulp fibers are derived from deciduous trees and include pulp fibers such as, but not limited to, eucalyptus, maple, birch, aspen, etc. Eucalyptus kraft pulp fibers may be particularly desired to increase softness, enhance brightness, increase opacity, and change the pore structure of the sheet to increase its wicking ability.

If desired, the moisture-holding layer may also contain synthetic fibers, such as monocomponent and multicomponent (e.g., bicomponent) fibers. Multicomponent fibers, for instance, are fibers formed from at least two thermoplastic polymers that are extruded from separate extruders, but spun together to form one fiber. In a sheath/core multicomponent fiber, a first polymer component is surrounded by a second polymer component. The polymers of the multicomponent fibers are arranged in substantially constantly positioned distinct zones across the cross-section of the fiber and extend continuously along the length of the fibers. Various combinations of polymers for the multicomponent fiber may be useful in the present invention, but the first polymer component typically melts at a temperature lower than the melting temperature of the second polymer component. Melting of the first polymer component allows the fibers to form a tacky skeletal structure, which upon cooling, captures and binds many of the pulp fibers. Typically, the polymers of the multicomponent fibers are made up of different thermoplastic materials, such as polyolefin/polyester (sheath/core) bicomponent fibers in which the polyolefin (e.g., polyethylene sheath) melts at a temperature lower than the core (e.g., polyester). Exemplary thermoplastic polymers include polyolefins (e.g. polyethylene, polypropylene, polybutylene, and copolymers thereof), polytetrafluoroethylene, polyesters (e.g. polyethylene terephthalate), polyvinyl acetate, polyvinyl chloride acetate, polyvinyl butyral, acrylic resins (e.g. polyacrylate, polymethylacrylate, and polymethylmethacrylate), polyamides (e.g., nylon), polyvinyl chloride, polyvinylidene chloride, polystyrene, polyvinyl alcohol, polyurethanes, cellulosic resins (e.g., cellulosic nitrate, cellulosic acetate, cellulosic acetate butyrate, and ethyl cellulose), and copolymers of any of the above materials, such as ethylene-vinyl acetate copolymers, ethylene-acrylic acid copolymers, styrene-butadiene block copolymers, and so forth.

The moisture-holding layer may also include a superabsorbent material, such as natural, synthetic and modified natural materials. Superabsorbent materials are water-swellable materials capable of absorbing at least about 20 times its weight and, in some cases, at least about 30 times its weight in an aqueous solution containing 0.9 weight percent sodium chloride. Examples of synthetic superabsorbent material polymers include the alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further superabsorbent materials include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and so forth. Mixtures of natural and wholly or partially synthetic superabsorbent polymers may also be useful in the present invention. Other suitable absorbent gelling materials are disclosed in U.S. Pat. Nos. 3,901,236 to Assarsson et al.; 4,076,663 to Masuda et al.; and 4,286,082 to Tsubakimoto et al., which are incorporated herein in their entirety by reference thereto for all purposes.

When utilized, the superabsorbent material may constitute from about 1 wt. % to about 40 wt. %, in some embodiments, from about 5 wt. % to about 30 wt. %, and in some embodiments, from about 10 wt. % to about 25 wt. % of the moisture-holding layer (on a dry basis). Likewise, multicomponent fibers may constitute from about 1 wt. % to about 30 wt. %, in some embodiments, from about 2 wt. % to about 20 wt. %, and in some embodiments, from about 5 wt. % to about 15 wt. % of the moisture-holding layer (on a dry basis). The cellulosic fibers may also constitute up to 100 wt. %, in some embodiments from about 50 wt. % to about 95 wt. %, and in some embodiments, from about 65 wt. % to about 85 wt. % of the moisture-holding layer (on a dry basis).

If desired, the evaporation rate of moisture from the moisture-holding layer may be controlled to achieve the desired heating profile. By controlling the evaporation rate, the desired amount of moisture may be released to the exothermic composition within a given period of time. For example, it is normally desired that the average "evaporation rate" of moisture from the moisture-holding layer is from about 0.05% to about 0.5%, in some embodiments from about 0.10% to about 0.25%, and in some embodiments, from about 0.15% to about 0.2% per minute. The "evaporation rate" is determined by measuring the weight of moisture-holding layer at a certain time, subtracting this measured weight from the initial wet weight of the layer, dividing this value by the initial wet weight, and then multiplying by 100. The evaporation rates are calculated for several different times and then averaged. The evaporation rate is determined in the present invention at a relative humidity of 51% and temperature of about 22° C. It should be understood that these relative humidity and temperature conditions are "initial" conditions in that they may vary during testing due to the increased presence of water vapor in the atmosphere.

In some embodiments, the desired evaporation rate of moisture is achieved by controlling the nature of the aqueous solution applied to the moisture-holding layer. Namely, the application of only water (vapor pressure of 23.7 mm Hg at 25° C.) to the moisture-holding layer may sometimes result in too great of an evaporation rate. Thus, a solute may be added to the aqueous solution to reduce its vapor pressure, i.e., the tendency of the water molecules to evaporate. At 25° C., for example, the solute may be added so that the aqueous solution added to the moisture-holding layer has an evaporation rate of less than 23.7 mm Hg, in some embodiments less than about 23.2 mm Hg, and in some embodiments, from about 20.0 mm Hg to about 23.0 mm Hg. One particularly suitable class of solutes includes organic and/or inorganic metal salts. The metal salts may contain monovalent (e.g., $Na^+$), divalent (e.g., $Ca^{2+}$), and/or polyvalent cations. Examples of preferred metal cations include the cations of sodium, potassium, calcium, aluminum, iron, magnesium, zirconium, zinc, and so forth. Examples of preferred anions include halides, chlorohydrates, sulfates, citrates, nitrates, acetates, and so forth. Particular examples of suitable metal salts include sodium chloride, sodium bromide, potassium chloride, potassium bromide, calcium chloride, etc. The actual concentration of the solute in the aqueous solution may vary depending on the nature of the solute, the particular configuration of the thermal device, and the desired heating profile. For example, the solute may be present in the aqueous solution in an amount from about 0.1 wt. % to about 25 wt. %, in some embodiments from about 1 wt. % to about 20 wt. %, and in some embodiments, from about 5 wt. % to about 15 wt. % of the solution.

In addition to controlling aspects of the aqueous solution, the moisture-holding layer itself may be selectively tailored to achieve the desired evaporation rate. For example, moisture-holding layers having a relatively low density and basis weight tend to release too great an amount of moisture in comparison to those having a higher density and basis weight. Without intending to be limited by theory, it is believed that such high density and high basis weight webs may have a lower porosity, thereby making it more difficult for moisture to escape from the layer over an extended period of time. Thus, in one embodiment of the present invention, the moisture-holding layer (e.g., airlaid web) may have a density of from about 0.01 to about 0.50, in some embodiments from about 0.05 to about 0.25, and in some embodiments, from about 0.05 to about 0.15 grams per cubic centimeters (g/cm³). The density is based on the oven-dry mass of the sample and a thickness measurement made at a load of 0.34 kilopascals (kPa) with a 7.62-cm diameter circular platen at 50% relative humidity and 23° C. In addition, the basis weight of the moisture-holding layer may be from about 50 to about 500 grams per square meter ("gsm"), in some embodiments from about 100 to about 300 gsm, and in some embodiments, from about 150 to about 300 gsm.

Other techniques may also be employed to achieve the desired evaporation rate of moisture from the moisture-holding layer. For example, superabsorbent materials are capable of swelling in the presence of an aqueous solution. Swelling increases the absorption capacity of the moisture-holding layer, but likewise reduces the evaporation rate of moisture as the materials exhibit a greater tendency to "hold onto" the water molecules. Thus, the evaporation rate may be increased by reducing the degree of swelling. One technique for reducing the degree of swelling of a superabsorbent material involves reducing the temperature of the aqueous solution to below ambient temperature, such as less than about 25° C., and in some embodiments, from about 5° C. to about 20° C. The degree of swelling of the superabsorbent material may also be reduced by incorporating one or more ionic compounds into the aqueous solution to increase its ionic strength. The ionic compounds may be the same as the solutes described above. The "ionic strength" of a solution may be determined according to the following equation:

$$I=0.5*\Sigma z_i^2 *m_i$$

wherein, $z_i$ the valence factor; and $m_i$ is the concentration. For example, the ionic strength of a solution containing 1 molar calcium chloride and 2 molar sodium chloride is "3" and determined as follows:

$$I=0.5*[(2^2*1)+(1^2*2)]=3$$

Without intending to be limited by theory, it is believed that superabsorbent materials have a counterion atmosphere surrounding the ionic backbone of the polymer chains that collapses when its ionic strength is increased. Specifically, the counterion atmosphere is made up of ions of opposite charge to the charges along the backbone of a superabsorbent polymer and are present in the ionic compound (e.g., sodium or potassium cations surrounding the carboxylate anions distributed along the backbone of a polyacrylate anionic polymer). As the concentration of ions contacting the superabsorbent polymer increases, the ion concentration gradient in the liquid phase from the exterior to the interior of the polymer begins to decrease and the counterion atmosphere thickness ("Debye thickness") may be reduced from about 20 nanometers (in pure water) to about 1 nanometer or less. When the counterion atmosphere is highly extended, the counterions are more osmotically active and therefore promote a higher degree of liquid absorbency. To the contrary, when the ion concentration in the absorbed liquid increases, the counterion atmosphere collapses and the absorption capacity is diminished. As a result of the reduction in absorption capacity, the superabsorbent material exhibits less of a tendency to hold the water molecules, thereby allowing its release to the exothermic composition.

The thermal device may also employ a breathable layer that is impermeable to liquids, but permeable to gases. This permits the flow of water vapor and air for activating the exothermic reaction, but prevents an excessive amount of liquids from contacting the thermal substrate, which could either suppress the reaction or result in an excessive amount of heat that overly warms or burns the user. The breathable layer may generally be formed from a variety of materials as is well known in the art. For example, the breathable layer may contain a breathable film, such as a microporous or monolithic film. The film may be formed from a polyolefin polymer, such as linear, low-density polyethylene (LLDPE) or polypropylene. Examples of predominately linear polyolefin polymers include, without limitation, polymers produced from the following monomers: ethylene, propylene, 1-butene, 4-methyl-pentene, 1-hexene, 1-octene and higher olefins as well as copolymers and terpolymers of the foregoing. In addition, copolymers of ethylene and other olefins including butene, 4-methyl-pentene, hexene, heptene, octene, decene, etc., are also examples of predominately linear polyolefin polymers.

If desired, the breathable film may also contain an elastomeric polymer, such as elastomeric polyesters, elastomeric polyurethanes, elastomeric polyamides, elastomeric polyolefins, elastomeric copolymers, and so forth. Examples of elastomeric copolymers include block copolymers having the general formula A-B-A' or A-B, wherein A and A' are each a thermoplastic polymer endblock that contains a styrenic moiety (e.g., poly(vinyl arene)) and wherein B is an elastomeric polymer midblock, such as a conjugated diene or a lower alkene polymer (e.g., polystyrene-poly(ethylene-butylene)-polystyrene block copolymers). Also suitable are polymers composed of an A-B-A-B tetrablock copolymer, such as discussed in U.S. Pat. No. 5,332,613 to Taylor, et al., which is incorporated herein in its entirety by reference thereto for all purposes. An example of such a tetrablock copolymer is a styrene-poly(ethylene-propylene)-styrene-poly(ethylene-propylene) ("S-EP-S-EP") block copolymer. Commercially available A-B-A' and A-B-A-B copolymers include several different formulations from Kraton Polymers of Houston, Tex. under the trade designation KRATON®. KRATON® block copolymers are available in several different formulations, a number of which are identified in U.S. Pat. Nos. 4,663,220, 4,323,534, 4,834,738, 5,093,422 and 5,304,599, which are hereby incorporated in their entirety by reference thereto for all purposes. Other commercially available block copolymers include the S-EP-S or styrene-poly(ethylene-propylene)-styrene elastomeric copolymer available from Kuraray Company, Ltd. of Okayama, Japan, under the trade name SEPTON®.

Examples of elastomeric polyolefins include ultra-low density elastomeric polypropylenes and polyethylenes, such as those produced by "single-site" or "metallocene" catalysis methods. Such elastomeric olefin polymers are commercially available from ExxonMobil Chemical Co. of Houston, Tex. under the trade designations ACHIEVE® (propylene-based), EXACT® (ethylene-based), and EXCEED® (ethylene-based). Elastomeric olefin polymers are also commercially available from DuPont Dow Elastomers, LLC (a joint venture between DuPont and the Dow Chemical Co.) under the trade designation ENGAGE® (ethylene-based) and AFFINITY® (ethylene-based). Examples of such polymers are also described in U.S. Pat. Nos. 5,278,272 and 5,272,236 to Lai, et al., which are incorporated herein in their entirety by reference thereto for all purposes. Also useful are certain elastomeric polypropylenes, such as described in U.S. Pat. Nos. 5,539,056 to Yanq, et al. and 5,596,052 to Resconi, et al., which are incorporated herein in their entirety by reference thereto for all purposes.

If desired, blends of two or more polymers may also be utilized to form the breathable film. For example, the film may be formed from a blend of a high performance elastomer and a lower performance elastomer. A high performance elastomer is generally an elastomer having a low level of hysteresis, such as less than about 75%, and in some embodiments, less than about 60%. Likewise, a low performance elastomer is generally an elastomer having a high level of hysteresis, such as greater than about 75%. The hysteresis value may be determined by first elongating a sample to an ultimate elongation of 50% and then allowing the sample to retract to an amount where the amount of resistance is zero. Particularly suitable high performance elastomers may include styrenic-based block copolymers, such as described above and commercially available from Kraton Polymers of Houston, Tex. under the trade designation KRATON®. Likewise, particularly suitable low performance elastomers include elastomeric polyolefins, such as metallocene-catalyzed polyolefins (e.g., single site metallocene-catalyzed linear low density polyethylene) commercially available from DuPont Dow Elastomers, LLC under the trade designation AFFINITY®. In some embodiments, the high performance elastomer may constitute from about 25 wt. % to about 90 wt. % of the polymer component of the film, and the low performance elastomer may likewise constitute from about 10 wt. % to about 75 wt. % of the polymer component of the film. Further examples of such a high performance/low performance elastomer blend are described in U.S. Pat. No. 6,794,024 to Walton, et al., which is incorporated herein in its entirety by reference thereto for all purposes.

As stated, the breathable film may be microporous. The micropores form what is often referred to as tortuous pathways through the film. Liquid contacting one side of the film does not have a direct passage through the film. Instead, a network of microporous channels in the film prevents liquids from passing, but allows gases and water vapor to pass. Microporous films may be formed from a polymer and a filler (e.g., calcium carbonate). Fillers are particulates or other forms of material that may be added to the film polymer extrusion blend and that will not chemically interfere with the extruded film, but which may be uniformly dispersed throughout the film. Generally, on a dry weight basis, based on the total weight of the film, the film includes from about 30% to about 90% by weight of a polymer. In some embodiments, the film includes from about 30% to about 90% by weight of a filler. Examples of such films are described in U.S. Pat. Nos. 5,843,057 to McCormack; 5,855,999 to McCormack; 5,932,497 to Morman, et al.; 5,997,981 to McCormack et al.; 6,002,064 to Kobylivker, et al.; 6,015,764 to McCormack, et al.; 6,037,281 to Mathis, et al.; 6,111,163 to McCormack, et al.; and 6,461,457 to Taylor, et al., which are incorporated herein in their entirety by reference thereto for all purposes.

The films are generally made breathable by stretching the filled films to create the microporous passageways as the polymer breaks away from the filler (e.g., calcium carbonate) during stretching. For example, the breathable material contains a stretch-thinned film that includes at least two basic components, i.e., a polyolefin polymer and filler. These components are mixed together, heated, and then extruded into a film layer using any one of a variety of film-producing processes known to those of ordinary skill in the film processing art. Such film-making processes include, for example, cast embossed, chill and flat cast, and blown film processes.

Another type of breathable film is a monolithic film that is a nonporous, continuous film, which because of its molecular structure, is capable of forming a liquid-impermeable, vapor-permeable barrier. Among the various polymeric films that fall into this type include films made from a sufficient amount of poly(vinyl alcohol), polyvinyl acetate, ethylene vinyl alcohol, polyurethane, ethylene methyl acrylate, and ethylene methyl acrylic acid to make them breathable. Without intending to be held to a particular mechanism of operation, it is believed that films made from such polymers solubilize water molecules and allow transportation of those molecules from one surface of the film to the other. Accordingly, these films may be sufficiently continuous, i.e., nonporous, to make them substantially liquid-impermeable, but still allow for vapor permeability.

Breathable films, such as described above, may constitute the entire breathable material, or may be part of a multilayer film. Multilayer films may be prepared by cast or blown film coextrusion of the layers, by extrusion coating, or by any conventional layering process. Further, other breathable materials that may be suitable for use in the present invention are described in U.S. Pat. Nos. 4,341,216 to Obenour; 4,758,239 to Yeo, et al.; 5,628,737 to Dobrin, et al.; 5,836,932 to Buell; 6,114,024 to Forte; 6,153,209 to Vega, et al.; 6,198,018 to Curro; 6,203,810 to Alemany, et al.; and 6,245,401 to Ying, et al., which are incorporated herein in their entirety by reference thereto for all purposes.

If desired, the breathable film may also be bonded to a nonwoven web, knitted fabric, and/or woven fabric using well-known techniques. For instance, suitable techniques for bonding a film to a nonwoven web are described in U.S. Pat. Nos. 5,843,057 to McCormack; 5,855,999 to McCormack; 6,002,064 to Kobylivker, et al.; 6,037,281 to Mathis, et al.; and WO 99/12734, which are incorporated herein in their entirety by reference thereto for all purposes. For example, a breathable film/nonwoven laminate material may be formed from a nonwoven layer and a breathable film layer. The layers may be arranged so that the breathable film layer is attached to the nonwoven layer. In one particular embodiment, the breathable material is formed from a nonwoven fabric (e.g., polypropylene spunbonded web) laminated to a breathable film.

Although various configurations of a thermal device have been described above, it should be understood that other configurations are also included within the scope of the present invention. For instance, other layers may also be employed to improve the exothermic properties of the thermal device. For example, a substrate may be used near or adjacent to the thermal substrate of the present invention that includes a coating of moisture-retaining particles. As described above, the moisture-retaining particles may retain and release moisture for activating the exothermic reaction. Furthermore, of particular benefit, one or more of the above-mentioned layers may accomplish multiple functions of the thermal device. For example, in some embodiments, the breathable layer, moisture-holding layer, etc., may be applied with an exothermic coating and thus also serve as a thermal substrate. Although not expressly set forth herein, it should be understood that numerous other possible combinations and configurations would be well within the ordinary skill of those in the art.

The above-described moisture-holding and/or breathable layers may generally be arranged in any desired position relative to the exothermic coating. In this regard, various configurations of the thermal device of the present invention will now be described in more detail. It should be understood, however, that the description below is merely exemplary, and that other thermal device configurations are also contemplated by the present inventors.

Referring to FIG. 1 for example, one embodiment of a thermal device 10 that may be formed in accordance with the present invention is shown. As shown, the thermal device 10 defines two outer surfaces 17 and 19, and is in the form of a substantially flat, conformable, and foldable material. The overall size and shape of the thermal device 10 are not critical. For example, the thermal device 10 may have a shape that is generally triangular, square, rectangular, pentagonal, hexagonal, circular, elliptical, etc. As shown, the thermal device 10 includes a thermal substrate 12 that contains one or more exothermic coatings. In this embodiment, breathable layers 14a and 14b are included within the thermal device 10 that are impermeable to liquids, but permeable to gases. It should be understood that, although shown herein as having two breathable layers, any number of breathable layers (if any) may be employed in the present invention. The thermal device 10 also includes a moisture-holding layer 16 that is configured to absorb and hold moisture for an extended period of time. The breathable layers 14a and 14b and the moisture-holding layer 16 may be positioned in various ways relative to the thermal substrate 12. In FIG. 1, for example, the breathable layers 14a and 14b are positioned directly adjacent to the thermal substrate 12. As a result, the breathable layers 14a and 14b may prevent external liquids from contacting the substrate 12 and may also control the amount of air that contacts the substrate 12 over a given period of time. The moisture-holding layer 16 may also be positioned in various locations, but is generally positioned to help facilitate the source of moisture for the thermal substrate 12. It should be understood that, although shown herein as having one moisture-holding layer, any number of layers (if any) may be employed in the present invention.

Although not specifically illustrated, the thermal device 10 may also include various other layers. For example, the thermal device 10 may employ a thermally conductive layer to help distribute heat toward the direction of a user (i.e., -z direction) and/or along the x-y plane of the device 10, thereby improving the uniformity of heat application over a selected area. The thermally conductive layer may have a coefficient of thermal conductivity of at least about 0.1 Watts per meter-Kelvin (W/m-K), and in some embodiments, from about 0.1 to about 10 W/m-k. Although any thermally conductive material may generally be employed, it is often desired that the selected material be conformable to enhance the comfort and flexibility of the device 10. Suitable conformable materials include, for instance, fibrous materials (e.g., nonwoven webs), films, and so forth. Optionally, the thermally conductive layer may be vapor-permeable so that air may contact the thermal substrate 12 when desired to activate the exothermic reaction. One type of vapor-permeable, conformable material that may be used in the thermally conductive layer is a nonwoven web material. For example, the thermally conductive layer may contain a nonwoven laminate, such as a spunbonded/meltblown/spunbonded ("SMS") laminate. Such SMS laminates may also provide liquid strike-through protection and breathability. The SMS laminate is formed by well-known methods, such as described in U.S. Pat. No. 5,213,881 to Timmons, et al., which is incorporated herein its entirety by reference thereto for all purposes. Another type of vapor-permeable, conformable material that may be used in the thermally conductive layer is a breathable film. For example, the thermally conductive layer may sometimes utilize a breathable film/nonwoven laminate.

A variety of techniques may be employed to provide conductivity to the thermally conductive layer. For example, a metallic coating may be utilized to provide conductivity. Metals suitable for such a purpose include, but are not limited to, copper, silver, nickel, zinc, tin, palladium, lead, copper, aluminum, molybdenum, titanium, iron, and so forth. Metallic coatings may be formed on a material using any of a variety of known techniques, such as vacuum evaporation, electrolytic plating, etc. For instance, U.S. Pat. Nos. 5,656,355 to Cohen; 5,599,585 to Cohen; 5,562,994 to Abba, et al.; and 5,316,837 to Cohen, which are incorporated herein their entirety by reference thereto for all purposes, describes suitable techniques for depositing a metal coating onto a material. Besides a metal coating, still other techniques may be employed to provide conductivity. For example, an additive may be incorporated into the material (e.g., fibers, film, etc.) to enhance conductivity. Examples of such additives include, but are not limited to, carbon fillers, such as carbon fibers and powders; metallic fillers, such as copper powder, steel, aluminum powder, and aluminum flakes; and ceramic fillers, such as boron nitride, aluminum nitride, and aluminum oxide. Commercially available examples of suitable conductive materials include, for instance, thermally conductive compounds available from LNP Engineering Plastics, Inc. of Exton, Pa. under the name Konduit® or from Cool Polymers of Warwick, R.I. under the name CoolPoly®. Although several examples of thermally conductive materials have been described above, it should be understood that any known thermally conductive material may be generally used in the present invention.

In addition to a thermally conductive layer, still other optional layers may be employed to enhance the effectiveness of the thermal device 10. For example, an insulation layer may be employed to inhibit heat dissipation to the outer environment so that heat is instead focused toward the patient or user. Because the insulation layer increases the overall heat-producing efficiency of the device 10, the desired temperature increase may be reached with a lower amount of exothermic coating or other reactant (i.e., moisture or oxygen). The insulation layer may have a coefficient of thermal conductivity of less than about 0.1 Watts per meter-Kelvin (W/m-K), and in some embodiments, from about 0.01 to about 0.05 W/m-k. Any known insulation material may be employed in the present invention. If desired, the selected insulation material may be fibrous in nature to improve the overall conformability of the thermal device 10. The fibrous material may possess high loft to enhance its insulative properties. Suitable high loft materials may include porous woven materials, porous nonwoven materials, etc. Particularly suitable high loft materials are nonwoven multicomponent (e.g., bicomponent) polymeric webs. For example, the multicomponent polymers of such webs may be mechanically or chemically crimped to increase loft. Examples of suitable high loft materials are described in more detail in U.S. Pat. Nos. 5,382,400 to Pike, et al.; 5,418,945 to Pike, et al. and 5,906,879 to Huntoon, et al., which are incorporated herein in their entirety by reference thereto for all purposes. Still other suitable materials for use as an insulation material are described in U.S. Pat. No. 6,197,045 to Carson, which is incorporated herein in its entirety by reference thereto for all purposes.

The thermal device 10 may also include layers that optionally form the outer surfaces 17 and 19, respectively, of the thermal device 10. These layers may present a compliant, soft feeling, and non-irritating surface to the user's skin. For example, the layers may be formed from materials that are liquid- and vapor-permeable, liquid-impermeable and vapor-permeable ("breathable"), and so forth. For example, the layers may be formed from a meltblown or spunbonded web of polyolefin fibers, as well as a bonded-carded, staple fiber, and/or hydraulically entangled web of natural and/or synthetic fibers. In another embodiment, the layers may be formed from a breathable nonwoven laminate (e.g., spunbond web/breathable film laminate), such as described above. The layers may further include a composition that is configured to transfer to the wearer's skin for improving skin health. Suitable compositions are described in U.S. Pat. No. 6,149,934 to Krzysik et al., which is incorporated herein in its entirety by reference thereto for all purposes.

The various layers and/or components of the thermal device 10 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In some embodiments, the exothermic coating may serve the dual purposes of generating heat and also acting as the adhesive. For example, the binder(s) of the exothermic coating may bond together one or more layers of the thermal device 10.

Figure 2:
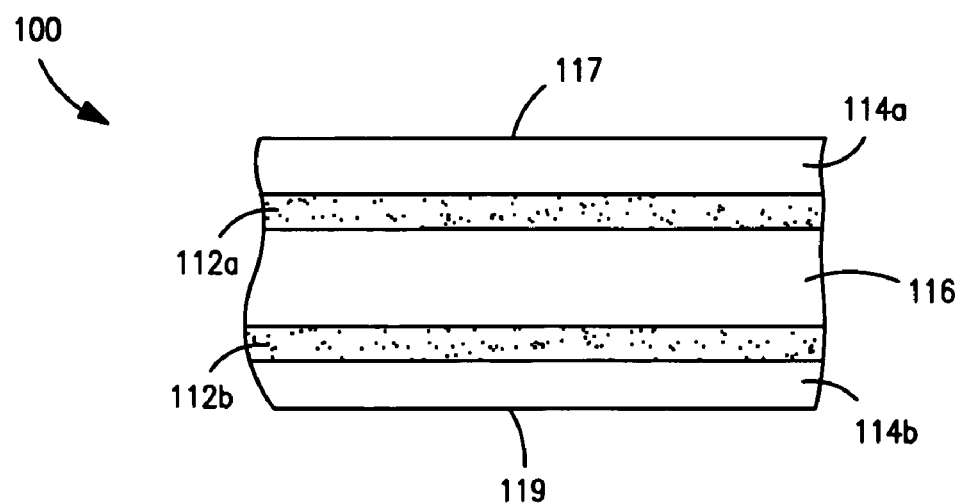
FIG. 2 illustrates a cross-sectional view of another embodiment of a thermal device that may be formed according to the present invention.

To further enhance the amount of heat generated by the thermal device, multiple thermal substrates may sometimes be employed. The multiple thermal substrates may be placed adjacent to one another or spaced apart by one or more layers. For example, referring to FIG. 2, one embodiment of a thermal device 100 is shown that contains a first thermal substrate 112a and a second thermal substrate 112b. Although not required, the thermal device 100 also includes a first breathable layer 114a and a second breathable layer 114b. The thermal device 100 also includes a moisture-holding layer 116 for facilitating the supply of moisture to the thermal substrates 112a and 112b. The moisture-holding layer 116 is positioned between the thermal substrate 112a/breathable layer 114a and the thermal substrate 112b/breathable layer 114b. In this manner, the amount of moisture supplied to each substrate is relatively uniform. It should be understood, however, that any placement, selection, and/or number of layers may be employed in the present invention.

As described above, certain aspects of the thermal device may be optimized to supply a controlled amount of moisture and/or oxygen to the exothermic coating during use. Through selective control over the supply of these reactants, a heating profile may be achieved in which an elevated temperature is reached quickly and maintained over an extended period of time. For example, an elevated temperature of from about 30° C. to about 60° C., in some embodiments from about 35° C. to about 55° C., and in some embodiments from about 37° C. to about 43° C., may be achieved in 20 minutes or less, and in some embodiments, 10 minutes or less. This elevated temperature may be substantially maintained for at least about 1 hour, in some embodiments at least about 2 hours, in some embodiments at least about 4 hours, and in some embodiments, at least about 10 hours (e.g., for overnight use).

Moisture may be applied any time prior to or during use of the thermal device, such as just prior to use or during manufacture. For example, water may be pre-applied to the moisture-holding layer as described above. The moisture is added in an amount effective to activate an exothermic, electrochemical reaction between the electrochemically oxidizable element (e.g., metal powder) and the electrochemically reducible element (e.g., oxygen). Although this amount may vary depending on the reaction conditions and the amount of heat desired, the moisture is typically added in an amount from about 20 wt. % to about 500 wt. %, and in some embodiments, from about 50 wt. % to about 200 wt. %, of the weight of the amount of oxidizable metal present in the coating. Although not necessarily required, it may be desired to seal such water-treated thermal devices within a substantially liquid-impermeable material (vapor-permeable or vapor-impermeable) that inhibits the exothermic coating from contacting enough oxygen to prematurely activate the exothermic reaction. To generate heat, the thermal device is simply removed from the package and exposed to air.

The thermal device of the present invention may be employed in a wide range of articles to provide a warming effect. For example, the thermal device may be used as a heating pad, bandage, food warmer, animal warmer, water warmer, and so forth. The thermal device may also be used to deliver warmth in various other applications, such as drapes or blankets for warming patients during surgical or medical procedures.

The present invention may be better understood with reference to the following examples.

EXAMPLE 1

The ability to form a thermal device in accordance with the present invention was demonstrated. Initially, a two-layer bonded carded web fabric was provided that had a basis weight of 75 grams per square meter (2.25 osy). One layer contained 0.5 osy of a 100% 1.5 denier FiberVisions (Covington, Ga.) ESC 215 bicomponent (PE sheath/PP core) fiber with 0.55% HR6 finish and the other layer contained 1.75 osy of a blend of 40% 15 denier Invista (Wichita, Kans.) T-295 polyester fiber with 0.50% L1 finish and 60% of a 28 denier FiberVisions ESC bicomponent (PE sheath/PP core) fiber with 0.55% HR6 finish.

The coating formulation was prepared as follows. In a 400 mL pyrex beaker, 5.0 grams of METOLOSE SM-100 (Shin-Etsu Chemical Co., Ltd.) and 3.7 grams of sodium chloride (Mallinckrodt) were added to 175.0 grams of distilled water that was stirred and heated to 71° C. The mixture was stirred and allowed to cool as the following additional ingredients were added sequentially: 17.8 grams of DUR-O-SET® Elite PE 25-220A ethylene-vinyl acetate emulsion (Celanese Emulsions), 43.8 grams of XP-5200-6 sample #05.2435503 calcium carbonate slurry (Omya), 9.0 grams of Nuchar SA-400 activated carbon (MeadWestvaco), and 170.1 grams of A-131 iron powder (North American Höganäs). After about 20 minutes of stirring the formulation with all ingredients, the temperature was reduced with an ice bath from about 24° C. to about 11° C. A noticeable increase in viscosity occurred when the temperature reached about 20° C. The viscosity of the formulation was measured at 1,950 cP (Brookfield Viscometer, LV-4 spindle at 60 rpm), and the percent solids were measured at 50.5% using a Sartorius (Edgewood, N.Y.) MA 30 solids analyzer. The calculated concentration of each component of the aqueous formulation is set forth below in Table 1.

TABLE 1

Components of the Aqueous Formulation

| Component | Calculated Amount |
|---|---|
| Iron | 40.1% |
| Activated Carbon | 2.1% |
| Methyl Cellulose ("MC") | 1.2% |
| Ethylene Vinyl-Acetate ("EVA") | 2.0% |
| Calcium Carbonate | 3.6% |
| Sodium Chloride | 0.9% |
| Water | 50.1% |

The aqueous formulation was applied to the polyester/bicomponent fiber side of the 75 gsm two-layer bonded carded web fabric using a #60 single wound Meyer rod. Pieces 6.5"×9" were coated and dried in an oven for about 1 hour at 110° C. The concentration of the components of the exothermic composition was then calculated from the coated and dried fabric pieces (19.7 grams), the untreated pieces of fabric (2.9 grams), and the composition of the aqueous formulation. The results are set forth below in Table 2.

TABLE 2

Components of the Exothermic Composition

| Component | Calculated Amount |
|---|---|
| Iron | 80.4% |
| Activated Carbon | 4.3% |
| Methyl Cellulose ("MC") | 2.4% |
| Ethylene Vinyl-Acetate ("EVA") | 4.1% |
| Sodium Chloride | 1.8% |
| Calcium Carbonate | 7.2% |
| Solids Add-On Level | ~575% |

A five-layered structure (2.8"×7") was then designed for activating the exothermic reaction. Specifically, the five-layered structure included one of the coated fabric pieces positioned on one side of a moisture holding layer, and another coated fabric piece positioned on the other side of the moisture holding layer. The uncoated side of the fabric pieces faced the moisture holding layer.

The moisture holding layer was formed from 75 wt. % wood pulp fluff, 15 wt. % superabsorbent, and 10 wt. % of KoSa T255 bicomponent fiber. The moisture holding layer had a basis weight of 225 grams per square meter and a density of 0.12 grams per cubic centimeter. The wood pulp fluff was obtained from Weyerhaeuser under the name "NB416." The superabsorbent was obtained from Degussa AG under the name "SXM 9543." A "separation layer" was used to separate the moisture holding layer from the coated layer on each side. The separation layer was a fabric/film laminate with small perforated holes for allowing vapor and gas to pass while preventing passage of liquid. It was obtained from Tredegar Film Products with the label FM-425 lot no. SHBT040060.

Prior to forming the multi-layered structure, the moisture holding layer was wetted on each side by spraying a total of 8.5 grams of an aqueous salt so that the weight of the original layer increased by a factor of 3.8. The salt solution contained 10.0 wt. % sodium chloride in distilled water. Then the separation layer was placed around it with the fabric side of the separation layer in contact with the wetted moisture holding layer. A coated layer was then placed on each side with the uncoated side in contact with the film side of the separation layer. The total weight of the two coated layers was 14.0 grams (9.6 grams of iron). The five-layered structure was then placed inside of a pouch (3.5"×8") that was sealed with a heat sealer. The pouch was made from a nylon spunbond microporous film laminate, obtained from Mitsubishi International Corp. and labeled TSF EDFH 5035-TYPE. The WVTR of the laminate was measured at 455±14 g/m$^2$/24 hrs (10 samples) by using the cup method (ASTM Standard E-96E-80). The pouch also contained an outer layer made of stapleknit fabric that was heat sealed to the nylon spunbond side of the TSF EDFH 5035-TYPE laminate. The stapleknit fabric was produced from 20% wood pulp fluff (50% Northern Softwood kraft fibers and 50% Alabama Pine bleached kraft softwood), 58% 1.5 denier polyester fiber (Invista Type 103), and 22% polypropylene spunbond (Kimberly-Clark Corp.). The resulting thermal device was stored in a metallized storage bag for 3 days prior to activating the reaction. The metallized storage bag was obtained from Kapak Corporation as KAL-ML5, a two-ply structure consisting of metallized polyester adhesively laminated to linear low density polyethylene.

EXAMPLE 2

The ability to form a thermal device in accordance with the present invention was demonstrated. A coating formulation similar to that described in Example 1 was prepared with xanthan gum in place of methylcellulose. Specifically, in a 400 mL pyrex beaker, 2.0 grams of xanthan gum (obtained from Cargill, Inc. as Verxan D) was added to 175.0 grams of room temperature distilled water that was stirred. After about 2.5 hours, the following ingredients were added sequentially to the stirring viscous solution: 3.7 grams sodium chloride (Mallinckrodt), 17.7 grams of DUR-O-SET® Elite PE 25-220A ethylene-vinyl acetate emulsion (Celanese Emulsions), 42.1 grams of XP-5200-6 sample #05.2435503 calcium carbonate slurry (Omya), 9.0 grams of Nuchar SA-400 activated carbon (MeadWestvaco), and 170.3 grams of A-131 iron powder (North American Höganäs). After about 2 hours of stirring the formulation with all ingredients, the viscosity was measured at 4,160 cP (Brookfield Viscometer, LV-4 spindle at 60 rpm), and the percent solids were measured at 51.2% using a Sartorius (Edgewood, N.Y.) MA 30 solids analyzer. The calculated concentration of each component of the aqueous formulation is set forth below in Table 3.

TABLE 3

Components of the Aqueous Formulation

| Component | Calculated Amount |
|---|---|
| Iron | 40.6% |
| Activated Carbon | 2.2% |
| Xanthan Gum ("XG") | 0.5% |
| Ethylene Vinyl-Acetate ("EVA") | 2.0% |
| Calcium Carbonate | 3.5% |
| Sodium Chloride | 0.9% |
| Water | 50.3% |

The aqueous formulation was applied to the polyester/bicomponent fiber side of the 75 gsm two-layer bonded carded web fabric described in EXAMPLE 1 using a #60 single wound Meyer rod. Pieces 6.5"×9" were coated and dried in an oven for about 40 minutes at 110° C. The concentration of the components of the exothermic composition was then calculated from the coated and dried fabric pieces (19.3 grams), the untreated pieces of fabric (2.9 grams), and the composition of the aqueous formulation. The results are set forth below in Table 4.

TABLE 4

Components of the Exothermic composition

| Component | Calculated Amount |
|---|---|
| Iron | 81.8% |
| Activated Carbon | 4.3% |
| Xanthan Gum ("XG") | 1.0% |
| Ethylene Vinyl-Acetate ("EVA") | 4.1% |
| Sodium Chloride | 1.8% |
| Calcium Carbonate | 7.0% |
| Solids Add-On Level | ~566% |

A five-layered structure (2.8"×7") as described in EXAMPLE 1 was then designed for activating the exothermic reaction. Specifically, the five-layered structure included one of the coated fabric pieces positioned on one side of a moisture holding layer. The moisture holding layer was wetted on each side by spraying a total of 8.9 grams of an aqueous salt solution so that the weight of the original layer increased by a factor of 3.8. The salt solution contained 10.0 wt. % sodium chloride in distilled water. Then the separation layer was placed around it with the fabric side of the separation layer in contact with the wetted moisture holding layer. A coated layer was then placed on each side with the uncoated side in contact with the film side of the separation layer. The total weight of the two coated layers was 13.9 grams (9.6 grams of iron). The five-layered structure was then placed inside of a pouch (3.5"×8") that was sealed with a heat sealer. The pouch was made from the nylon spunbond microporous film laminate, described in EXAMPLE 1. The pouch also contained the outer layer of stapleknit fabric as described in EXAMPLE 1. The resulting thermal device was stored in a metallized storage bag for 3 days prior to activating the reaction. The metallized storage bag was obtained from Kapak Corporation as KAL-ML5, a two-ply structure consisting of metallized polyester adhesively laminated to linear low density polyethylene.

EXAMPLE 3

The ability to form a thermal device in accordance with the present invention was demonstrated. Initially, a 7"-wide roll of a 2.25 osy dual layer bonded carded web (one side contains 0.5 osy of a 100% 1.5 denier FiberVisions ESC 215 bicomponent (PE sheath/PP core) fiber with 0.55% HR6 finish and the other side contains 1.75 osy of a blend of 40% 15 denier Invista T-295 polyester fiber with 0.50% L1 finish and 60% of a 28 denier FiberVisions ESC bicomponent (PE sheath/PP core) fiber with 0.55% HR6 finish) was coated on the polyester/bicomponent fiber side.

The coating formulation was prepared as follows. In a 2-gallon metal pail, 46.0 grams of METOLOSE SM-100 (Shin-Etsu Chemical Co., Ltd.) and 115.0 grams of sodium chloride (Mallinckrodt) were added to 1551.0 grams of distilled water that was stirred and heated to 69° C. The mixture was stirred and allowed to cool as the following additional ingredients were added sequentially: 178.1 grams of DUR-O-SET® Elite PE 25-220A ethylene-vinyl acetate emulsion (Celanese Emulsions), 440.6 grams of XP-5200-6 sample #05.2435503 calcium carbonate slurry (Omya), 92.1 grams of Nuchar SA-20 activated carbon (MeadWestvaco), and 1575.2 grams of A-131 iron powder (North American Höganäs). After about 75 minutes of stirring the formulation with all ingredients, the temperature was reduced with an ice bath from about 33° C. to about 15° C. A noticeable increase in viscosity occurred when the temperature was reduced. The calculated concentration of each component of the aqueous formulation is set forth below in Table 5.

TABLE 5

Components of the Aqueous Formulation

| Component | Calculated Amount |
|---|---|
| Iron | 39.4% |
| Activated Carbon | 2.3% |
| Methyl Cellulose ("MC") | 1.2% |
| Ethylene Vinyl-Acetate ("EVA") | 2.2% |
| Calcium Carbonate | 3.8% |
| Sodium Chloride | 2.9% |
| Water | 48.2% |

The aqueous formulation was applied to the polyester/bicomponent fiber side of the dual layer bonded carded web fabric in a pilot line process using a knife coater. A 0.75 osy spunbond-meltblown-spunbond fabric was used as a carrier sheet to support the coated dual layer bonded carded web and to also keep the coating formulation from bleeding through and contacting the components of the pilot coater (e.g. rollers). The gap between the knife and steel roller that carried the fabric was set at 900 micron. The line speed was 0.25 meters per minute. The pilot line coater contained a four-foot drier set at 145° C. that was used to partially dry the coated fabric. The partially dried coated fabric was cut into 15-inch pieces and placed in a laboratory oven at 110° C. for about 20 minutes to complete the drying step. The concentration of the components of the exothermic composition was calculated from the coated and dried fabric pieces (49.6±2.9 grams), the untreated piece of fabric (4.0 grams), and the composition of the aqueous formulation. The results are set forth below in Table 6.

TABLE 6

Components of the Exothermic Composition

| Component | Calculated Amount |
|---|---|
| Iron | 76.3% |
| Activated Carbon | 4.5% |
| Methyl Cellulose ("MC") | 2.2% |
| Ethylene Vinyl-Acetate ("EVA") | 4.2% |
| Sodium Chloride | 5.6% |
| Calcium Carbonate | 7.3% |
| Solids Add-On Level | ~1140% |

A five-layered structure (3"×3.5") was then designed for activating the exothermic reaction. Specifically, the five-layered structure included one of the coated fabric pieces positioned on one side of a moisture holding layer, and another coated fabric piece positioned on the other side of the moisture holding layer. The uncoated side of the fabric pieces faced the moisture holding layer. The moisture holding layer was formed from 75 wt. % wood pulp fluff, 15 wt. % superabsorbent, and 10 wt. % of KoSa T255 bicomponent fiber. The moisture holding layer had a basis weight of 225 grams per square meter and a density of 0.12 grams per cubic centimeter. The wood pulp fluff was obtained from Weyerhaeuser under the name "NB416." The superabsorbent was obtained from Degussa AG under the name "SXM 9543." A "separation layer" was used to separate the moisture holding layer from the coated layer on each side. The separation layer was a fabric/film laminate with small perforated holes for allowing vapor and gas to pass while preventing passage of liquid. It was obtained from Tredegar Film Products with the label FM-425 lot no. SHBT040060.

Prior to forming the multi-layered structure, the moisture holding layer was wetted by spraying 5.0 grams of an aqueous salt solution (10.0% sodium chloride in distilled water) to both sides so that the weight of the original layer increased by a factor of 3.9. Then the separation layer was placed around it with the fabric side of the separation layer in contact with the wetted moisture holding layer. A coated layer was then placed on each side with the uncoated side in contact with the film side of the separation layer. The total weight of the two coated layers was 11.6 grams (8.1 grams of iron). The five-layered structure was then placed inside of a pouch (4.2"×8.5") and the edges were heat sealed. The pouch was made of a nylon spunbond microporous film laminate. The laminate was obtained from Mitsubishi International Corp. and labeled TSF EDFH 5035-TYPE. The WVTR of the laminate was measured at 455 g/m²/24 hrs by using the cup method (ASTM Standard E-96E-80). The pouch also contained a layer of stapleknit fabric heat sealed to the nylon spunbond side. The stapleknit fabric was produced from 20% wood pulp fluff (50% Northern softwood kraft fibers and 50% Alabama Pine bleached kraft softwood), 58% 1.5 denier polyester fiber (Invista Type 103), and 22% polypropylene spunbond (Kimberly-Clark Corp.). The resulting thermal device was stored in a metallized storage bag for 25 hours prior to activating the reaction. The metallized storage bag was KAL-ML5, a two-ply structure consisting of metallized polyester adhesively laminated to linear low density polyethylene, obtained from Kapak Corporation.

EXAMPLE 4

A thermal device was formed as described in Example 3, except that the moisture holding layer was applied with 5.2 grams of an aqueous salt solution so that the weight of the original layer increased by a factor of 4.0. The salt solution contain 10.0 wt. % sodium chloride in distilled water. The total weight of the two coated layers was 11.7 grams (8.2 grams of iron). The resulting thermal device was stored in a metallized storage bag for 25 hours prior to activating the reaction.

EXAMPLE 5

Figure 3:
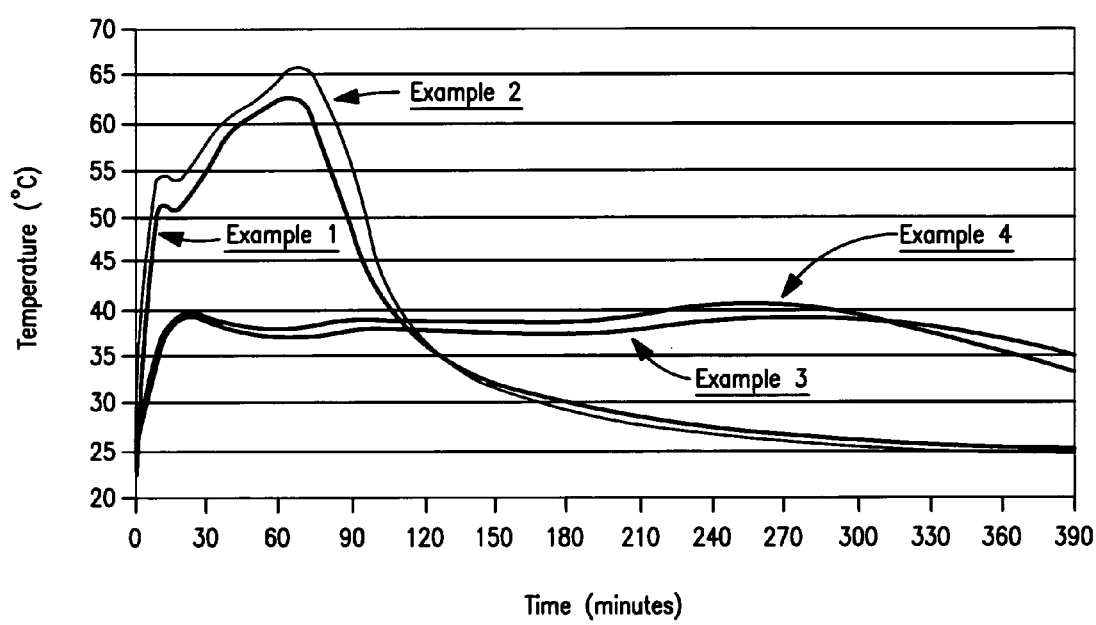
FIG. 3 is a thermal response curve showing temperature (° C.) versus time (minutes) for the samples of Example 1.

The ability to achieve a controlled heating profile using a thermal device with a durable exothermic coating of the present invention was demonstrated. Specifically, the thermal devices of Examples 1-4 were tested. The metallized storage bag was opened to initiate the reaction. Testing was conducted by attaching a thermocouple wired to a data collection device to one side of the thermal device. The temperature was recorded as a function of time (at 5-second intervals) to give the thermal curves shown in FIG. 3. As shown, a durable exothermic fabric was used in a warming device to produce a thermal response curve that reaches a higher temperature (e.g. 50-65° C.) for a shorter time period or a lower temperature (e.g., 37-40° C.) for a longer time period. Also, comparing Examples 1 and 2, the type of polysaccharide used in the coating formulation did not affect the thermal response curve.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A substrate containing an exothermic coating that is activatable to generate heat, wherein the exothermic coating is present at a solids add-on level of from about 20% to about 5000%, the exothermic coating comprising an oxidizable metal, a polymer latex and polysaccharide, the polymer latex having a glass transition temperature of about 30° C. or less, wherein the polymer latex constitutes from about 0.01 wt. % to about 20 wt. % of the exothermic coating and the polysaccharide constitutes from about 0.01 wt. % to about 20 wt. % of the exothermic coating, further wherein the weight ratio of the polymer latex to the polysaccharide is from about 0.5:1 to about 5:1, wherein the polymer latex is crosslinked and substantially insoluble in water, and wherein the exothermic coating is generally free of liquid water prior to activation.

2. The substrate of claim 1, wherein the glass transition temperature of the polymer latex is greater than about −25° C.

3. The substrate of claim 2, wherein the glass transition temperature of the polymer latex is from about −15° C. to about 15° C.

4. The substrate of claim 1, wherein the polymer latex is crosslinked without the aid of a crosslinking agent.

5. The substrate of claim 1, wherein the polymer latex contains an ethylene vinyl-acetate copolymer.

6. The substrate of claim 1, wherein the polysaccharide is a nonionic cellulosic ether.

7. The substrate of claim 6, wherein the nonionic cellulosic ether is selected from the group consisting of alkyl cellulose ethers, hydroxyalkyl cellulose ethers, alkyl hydroxyalkyl cellulose ethers, and combinations thereof.

8. The substrate of claim 1, wherein the polymer latex constitutes from about 0.5 wt. % to about 10 wt. % of the exothermic coating.

9. The substrate of claim 1, wherein the polysaccharide constitutes from about 0.5 wt. % to about 10 wt. % of the exothermic coating.

10. The substrate of claim 1, wherein the weight ratio of the polymer latex to the polysaccharide is from about 1:1 to about 3:1.

11. The substrate of claim 1, wherein the metal is iron zinc, aluminum, magnesium, or a combination thereof.

12. The substrate of claim 1, wherein the exothermic coating further comprises a carbon component.

13. The substrate of claim 12, wherein the carbon component includes activated carbon.

14. The substrate of claim 1, wherein the exothermic coating is present at solids add-on level of from about 100% to about 1200%.

15. The substrate of claim 1, wherein the substrate contains a nonwoven web.

16. The substrate of claim 1, wherein the metal is in the form of a powder that constitutes from about 40 wt. % to about 95 wt. % of the exothermic coating.

17. The substrate of claim 12, wherein the exothermic coating further comprises an electrolytic salt.

18. The substrate of claim 17, wherein the carbon component constitutes from about 1 wt. % to about 50 wt. % of the coating and the electrolytic salt constitutes from about 0.01 wt. % to about 10 wt. % of the coating.

19. The substrate of claim 17, wherein the carbon component constitutes from about 2 wt. % to about 30 wt. % of the exothermic coating and the electrolytic salt constitutes from about 0.1 wt. % to about 8 wt. % of the exothermic coating.

20. The substrate of claim 17, wherein the electrolytic salt is a metal halide.

21. A thermal device comprising a substrate containing an exothermic coating that is activatable to generate heat, wherein the exothermic coating is present at a solids add-on level of from about 20% to about 5000%, the exothermic coating comprising an oxidizable metal, a polymer latex and polysaccharide, the polymer latex having a glass transition temperature of about 30° C. or less, wherein the polymer latex constitutes from about 0.01 wt. % to about 20 wt. % of the exothermic coating and the polysaccharide constitutes from about 0.01 wt. % to about 20 wt. % of the exothermic coating, further wherein the weight ratio of the polymer latex to the polysaccharide is from about 0.5:1 to about 5:1, wherein the polymer latex is crosslinked and substantially insoluble in water, and wherein the exothermic coating is generally free of liquid water prior to activation.

22. The thermal device of claim 21, further comprising a moisture-holding layer and an aqueous solution applied to the moisture-holding layer that is capable of supplying moisture to the exothermic coating.

23. The thermal device of claim 22, further comprising a breathable layer capable of regulating the amount of moisture and oxygen contacting the exothermic coating.

24. The thermal device of claim 23, wherein the breathable layer is positioned between the substrate and the moisture holding layer.

* * * * *

UNITED STATES PATENT AND TRADEMARK OFFICE
CERTIFICATE OF CORRECTION

| | |
|---|---|
| PATENT NO. | : 7,686,840 B2 |
| APPLICATION NO. | : 11/303005 |
| DATED | : March 30, 2010 |
| INVENTOR(S) | : Roger Bradshaw Quincy, III et al. |

It is certified that error appears in the above-identified patent and that said Letters Patent is hereby corrected as shown below:

Claim 11 reads "...wherein the metal is iron zinc, aluminum,..." should read --...wherein the metal is iron, zink, aluminum...--.

Signed and Sealed this

Thirtieth Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,686,840 B2 | Page 1 of 1 |
| APPLICATION NO. | : 11/303005 | |
| DATED | : March 30, 2010 | |
| INVENTOR(S) | : Roger Bradshaw Quincy, III et al. | |

It is certified that error appears in the above-identified patent and that said Letters Patent is hereby corrected as shown below:

Claim 11, Column 27, lines 23-24 reads "...wherein the metal is iron zinc, aluminum,..." should read --...wherein the metal is iron, zink, aluminum...--.

This certificate supersedes the Certificate of Correction issued November 30, 2010.

Signed and Sealed this
Eighth Day of February, 2011

David J. Kappos
*Director of the United States Patent and Trademark Office*